United States Patent [19]

Bliss

[11] Patent Number: 5,750,878

[45] Date of Patent: May 12, 1998

[54] REMOVABLE REFERENCE PLATE

[75] Inventor: Brian Joseph Bliss, Ypsilanti, Mich.

[73] Assignee: Harbison-Walker Refractories Company, Pittsburgh, Pa.

[21] Appl. No.: 597,052

[22] Filed: Feb. 5, 1996

[51] Int. Cl.⁶ .................................................. G01N 3/62
[52] U.S. Cl. ........................... 73/1.79; 33/502; 356/375
[58] Field of Search ........................... 73/1 J, 1 R, 1.79, 73/1.01; 356/375; 33/502, 520, DIG. 21

[56] References Cited

U.S. PATENT DOCUMENTS

| | | | |
|---|---|---|---|
| 579,555 | 3/1897 | Collins | 33/293 |
| 704,631 | 7/1902 | Goodale | 33/293 |
| 913,069 | 2/1909 | Stephenson | 33/293 |
| 3,599,336 | 8/1971 | Walsh | 33/293 X |
| 3,734,627 | 5/1973 | Edwards | 356/399 X |
| 4,615,618 | 10/1986 | Bailey et al. | 356/155 X |
| 4,630,379 | 12/1986 | Wickmann et al. | 33/600 X |
| 4,840,490 | 6/1989 | Gabriel et al. | 356/375 |
| 5,125,745 | 6/1992 | Neiheisel et al. | 356/372 |
| 5,127,736 | 7/1992 | Neiheisel | 356/376 |
| 5,443,537 | 8/1995 | Haskins | 33/193 |

OTHER PUBLICATIONS

Keuffel & Esser Company brochure entitled "Optical Alignment Equipment", 2 pages 1974.

*Patent Abstracts of Japan* Grp. P1672, vol. 18, No. 14 Abs pub date Jan. 11, 1994 (5–256601) "Method and Device for Detecting Center Position of Circular Pipe" by Ichiro Kadowaki.

*Primary Examiner*—Thomas P. Noland
*Attorney, Agent, or Firm*—Craig G. Cochenour; John L. Sigalos

[57] ABSTRACT

A removable reference laser target for detachable installation at identified target positions on the exterior of a refractory lined high temperature molten metal vessel. The target includes a generally rectangular target plate with an elongated slot generally paralleling the long dimension of the rectangle. On the same side of the plate but on opposite sides of the slot are two mounting and adjusting bolts for detachably affixing the target at an identified position on the exterior surface of the vessel. Extending essentially at right angles to the major rectangular surface of the plate is an extension, the free end of which contacts an external reinforcing member and assures precise re-location of the target to be used with laser equipment to provide a reference for determining thickness and/or condition of a refractory lining of the vessel.

9 Claims, 3 Drawing Sheets

REMOVABLE REFERENCE PLATE

This invention relates to measurement of wear of high temperature refractories and more particularly to utilization of laser techniques for identifying and quantifying refractory wear.

BACKGROUND OF THE INVENTION

It is well known that refractories utilized in harsh environments such as those encountered in steel making are subject to high levels of wear and that great care must be taken to prevent break-outs through refractory walls such as those of steel-making ladles and other vessels.

Because the interior of such vessels typically are heated to about 1,650 degrees Celsius (about 3,000 degrees fahrenheit), it is not practicable to use many conventional techniques, some of which require cool-down, a condition that involves passage of considerable time. Moreover, if such a vessel is cooled to a state in which it is practicable to visually inspect it, a large quantity of heat must be re-imparted in order to return the interior to working temperature, thus contributing to inefficient use and increased expense in making/handling of steel. Accordingly, one attractive feature desired in monitoring refractory wear is that it can be carried out immediately after each use and without requiring substantial cooling. One technique that meets such criteria is that of laser monitoring and examination. However, for such to be accurate and dependable it is desirable that there be a plurality of reference targets precisely positioned in known locations with respect to the steel shell of the vessel so that laser measurements can be properly referenced to provide meaningful and accurate information identifying refractory wear or failure.

To use a laser system for measuring lining wear profiles, provision must be made for precisely defining the relative spatial locations of the laser gun and the vessel being measured. The vessel typically is disposed horizontally on a ladle car, and laser targets are located in a plane parallel to the mouth of the vessel. To precisely define relative spatial locations, these reference marks or targets have been located at several visible points on the vessel so that by measuring angles and distances, the relative locations can be determined. A laser profile is taken of the unlined inner vessel shell. This profile is then stored electronically and used as a base reference for subsequent measurements of the actual lining. The differentials between "clean" shell readings and used lining readings are plotted to provide a measure of wear.

It will thus be seen that due to the nature of laser techniques, it has been necessary for such reference targets to be precisely positioned, and thus it has been the practice to weld or otherwise permanently affix targets to precise locations on the exterior surfaces of shells of vessels. Thereupon, once the equipment and targets were calibrated, thicknesses of the interior refractory layers could be accurately determined.

Although the foregoing procedure has permitted accurate monitoring of refractory condition, problems have occurred with its use. Thus, the severe service conditions in which heavy steel-making vessels are subjected has often resulted in damage to the targets thus requiring tedious and laborious repair, replacement and re-calibration. While such is being done, the vessel is out of service. Accordingly, there has continued to be a need for techniques that protect the targets from damage while continuing to permit unrestricted use of the vessels involved.

BRIEF SUMMARY OF THE INVENTION

The improvement according to the invention hereof includes the provision of special removable laser targets that are used in cooperative combination with dedicated supports on the exterior surfaces of the vessel shells so that during use of the vessels the targets are safe from damage and yet are easily and quickly positionable at predetermined locations on shell exteriors to provide the needed target reference points when the laser refractory-measuring techniques are to be practiced. The targets are each comprised of a special mounting plate having a slot for mating engagement with one of a plurality of exterior ribs or dedicated flanges on the vessel shell exterior surfaces. Extending essentially at right angles to the major surface of the mounting plate is an elongated extension (locator rod). Typically, three or four such target assemblies are individually positioned, one on each of a corresponding plurality of ribs or flanges so as to provide three or four separate targets spaced from each other and appropriately located to provide the needed reference for the laser equipment.

In practice, while a ladle is being used, the target assemblies are kept in a safe place where they are not subject to damage, but are readily and quickly mountable at the precisely needed locations on the exterior surface of the vessel when measurements of refractory wear are to be made. As soon as such measurements are completed, the targets are quickly and easily detached for storage until needed again.

OBJECTS AND FEATURES OF THE INVENTION

It is one general object of the invention to improve monitoring and maintenance of refractory linings in high temperature steel-making vessels.

It is another object of the invention to safeguard associated laser orientation targets from damage.

It is still another object of the invention to facilitate ready installation and removal of laser targets from steel-making vessels.

Accordingly, in accordance with one feature of the invention, a plurality of individual laser target assemblies are provided, each having mounting bolts for temporary attachment and precision adjustment on the exterior of the vessel shells, thus providing for mounting at precisely located positions.

In accordance with another feature of the invention, the special mounting plates each have a slot for mating engagement with one of a plurality of exterior ribs or dedicated flanges on the vessel shell exterior surfaces, thus facilitating attachment and detachment.

In accordance with still another feature of the invention, a tubular extension projects essentially at right angles to the major surface of each mounting plate and target to facilitate precise relocation of the target relative to the vessel shell.

These and other objects and features of the invention will be apparent from the following description, by way of example of a preferred embodiment, with reference to the drawing.

DESCRIPTION OF A PREFERRED EMBODIMENT

Figure 1:
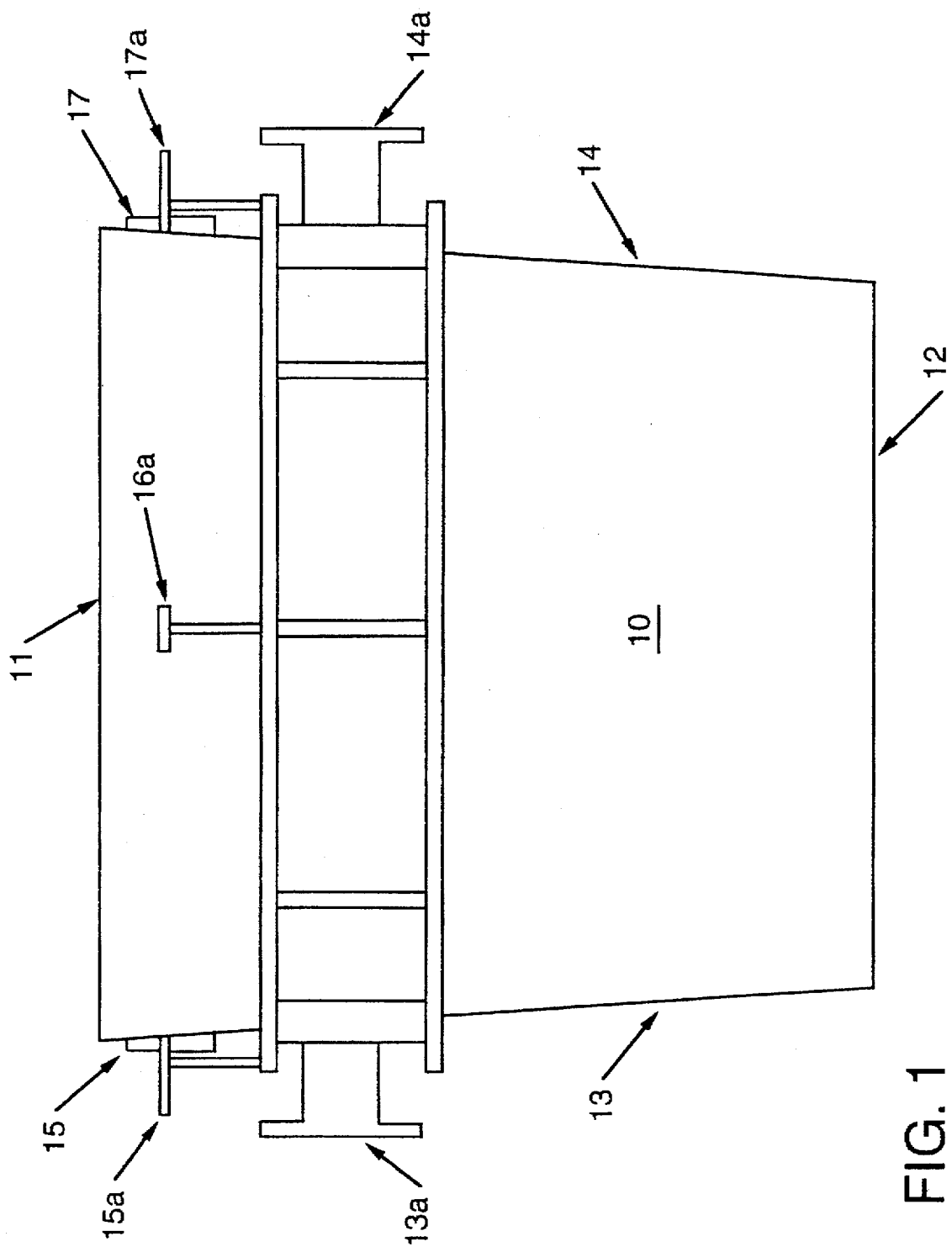
FIG. 1 is simple elevation depicting a typical ladle used in steel making and showing flanges thereon provided for cooperative association with the laser targets.

Now turning to the drawing, and more particularly FIG. 1 thereof, it will be seen to depict a typical steel-making vessel such as a conventional ladle 10 having a top 11, bottom 12, left side 13 and right side 14. Attached to left side 13 and right side 14 are trunions 13a and 14a for engagement with conventional lifting, transporting and manipulating equipment (not shown). Welded or otherwise permanently attached to the exterior steel shell are laser target mounting flanges or ribs 15, 16 and 17. (To improve clarity, flange 16 is not shown on FIG. 1). It should be noted that most commonly, steel ladles are oriented horizontally during laser scanning of the refractory lining.

Figure 2:
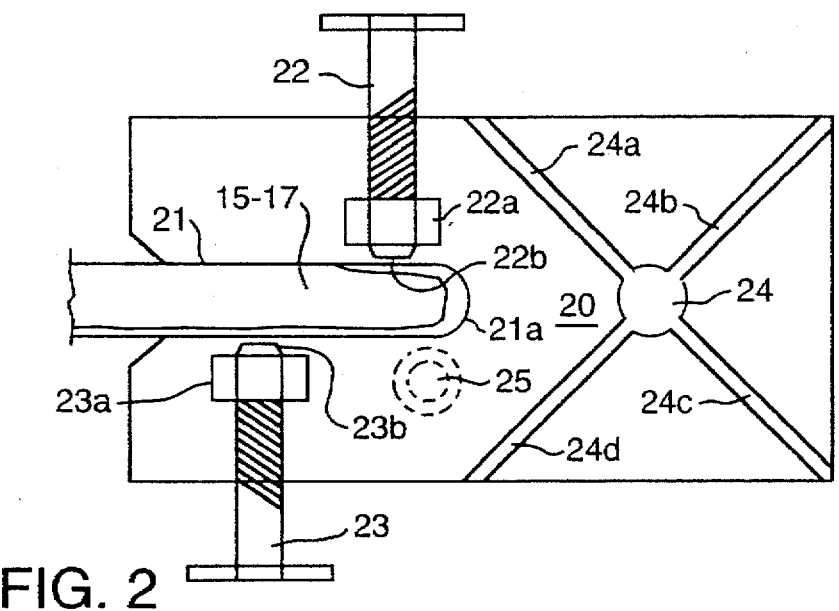
FIG. 2 is a "top" view of the laser target assembly showing a pair of bolts included to precisely secure the target to a rib or flange on the external steel shell.

Now turning to FIG. 2, a "top" view of the laser target assembly is depicted. There are seen the aforementioned special rectangular plate 20 having a generally rectangular slot 21 with rounded inner end 21a. Shown as captured within slot 21 is a part of one of the above-described flanges or ribs 15-17 to which plate 20 is attached by tightening mounting bolts 22 and 23. Nuts 22a and 23a are affixed to plate 20 as by welding or other conventional means so that turning bolts 22 and 23 respectively urge their inner ends 22b and 23b against adjacent surfaces of flange/ribs 15-17 and removably and adjustably lock plate 20 in place thereupon.

Further reference to FIG. 2 reveals shallow channels (saw cuts) 24a-24d which are configured in the shape of a St. Andrews Cross at the center of which is a shallow generally circular indentation 24 to assist visual sighting of the various reference targets. Thus, indentation 24 serves to locate a central reference point of target plate 20.

Figure 3:
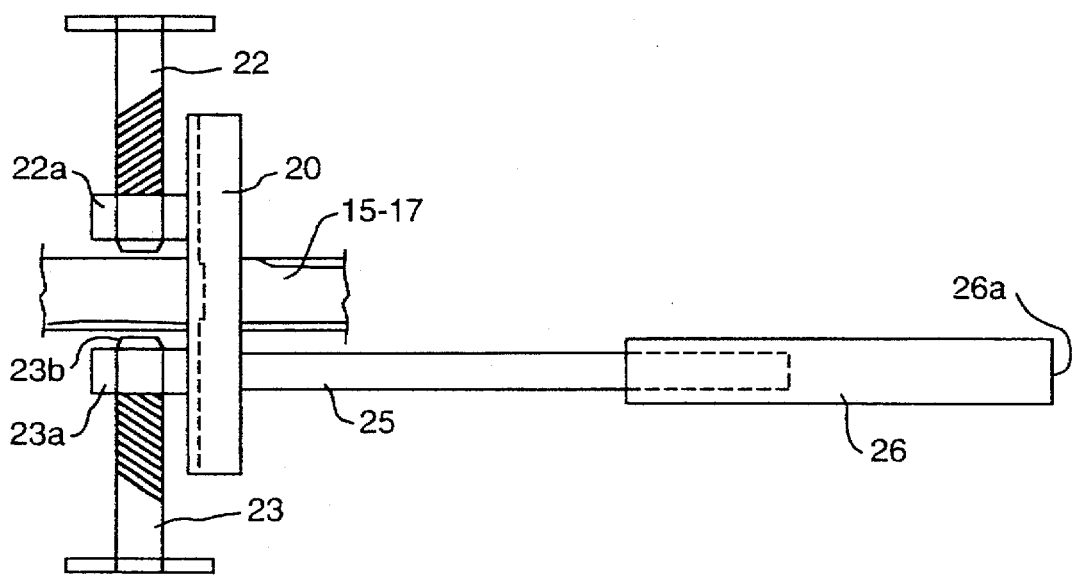
FIG. 3 is a side view of the laser target assembly of FIG. 2.

Now turning to FIG. 3, a side view of the target assembly of FIG. 2 is depicted. There, it will be observed, are flanges/ribs 15-17 together with members 20, 22, 22a, 23, 23a, 25 and 26. Members 25 and 26 comprise an extending locator rod affixed to supporting plate 20. When in position, the free end 26a of this locator rod 25/26 is in contact with another external reinforcing band (not shown) which is attached to the shell perpendicular to the ribs or flanges 15, 16, 17.

Figure 4:
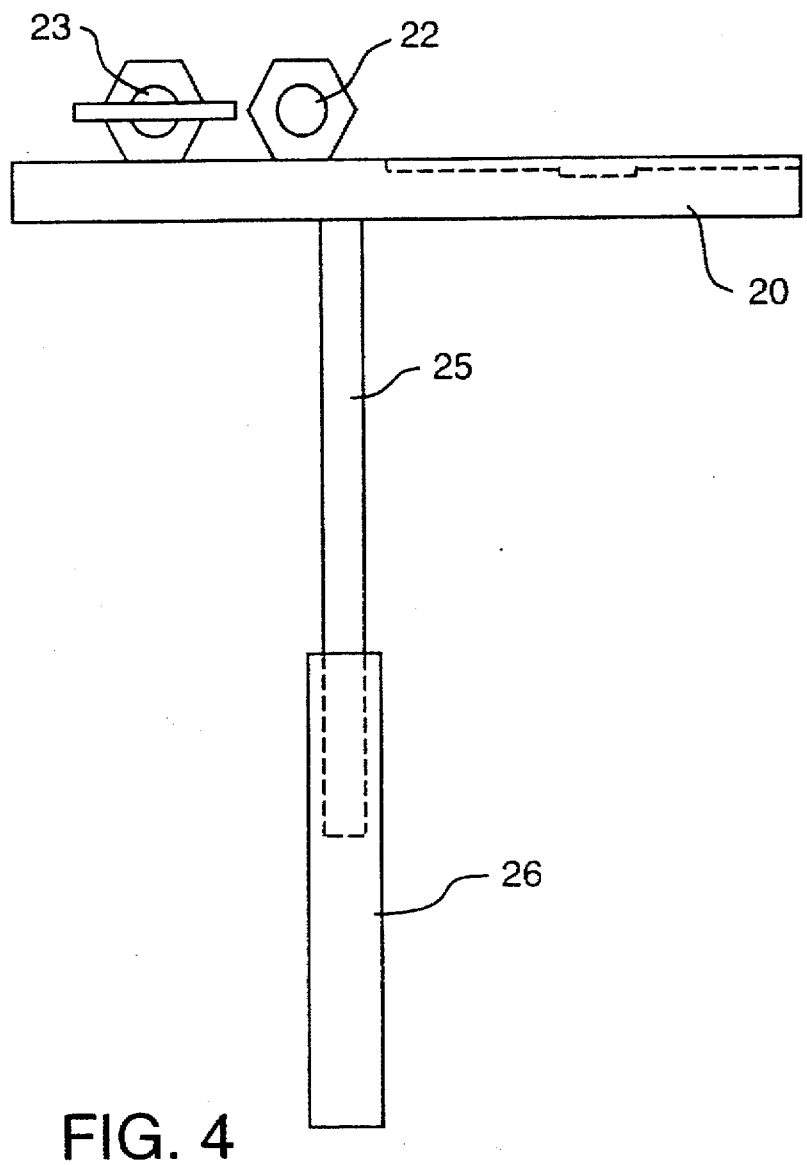
FIG. 4 is a another side view taken at right angles to the side view of FIG. 3.

FIG. 4 is another side view of FIG. 2 taken at right-angles to FIG. 3. There, to facilitate clarity in illustration of the target assembly, the flanges or ribs 15-17 are not shown, and the offset positioning of attachment/adjustment bolts 22 and 23 are clearly seen. Further, it should be noted that extending portion 26 of the composite locator rod 25/26 can be threaded onto inward portion 25 and thus provide a ready way of adjusting the total extending dimension thereof.

It will now be evident that there has been described herein an improved combination laser target support and target assembly.

Although the inventions hereof have been described by way of a preferred embodiment, it will be evident that other adaptations and modifications may be employed without departing from the spirit and scope thereof.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. A removable laser target reference assembly for temporary mounting on an exterior shell of a high temperature refractory lined steel making vessel wherein said vessel includes on an exterior surface thereof a pair of flange/ribs, said assembly comprising, in combination:

(a) a laser target having a mounting slot therein for mounting engagement with one of said flange/ribs; and (b) mounting means including a locator rod mounted on said laser target for engaging another of said flanges/ribs to accurately position said laser target.

2. A removable laser target reference assembly according to claim 1 wherein said mounting means includes a pair of offset bolts on a same side of said target for mounting said target on said one of said flanges/ribs of said shell.

3. A removable laser target reference assembly according to claim 1 wherein said target is elongated and said slot lies generally parallel to an elongate axis of the elongation.

4. A removable laser target reference assembly according to claim 3 wherein said mounting means includes a pair of offset bolts on a same side of said target for adjustably mounting said target on said one of said flanges/ribs of said shell.

5. A removable laser target reference assembly according to claim 1 wherein said locator rod is elongated and adjustably extends from the laser target.

6. A removable laser target reference assembly according to claim 5 wherein the elongated rod includes a free end and wherein when said assembly is emplaced upon said vessel, said free end engages said another of said flanges/ribs to accurately position said laser target.

7. A removable laser target reference assembly according to claim 5 wherein the elongated locator rod extends from said target at substantially right angles thereto.

8. A combination according to claim 1 wherein said slot of said removable laser target reference assembly removably mounts the target onto said one of said flanges/ribs.

9. A combination according to claim 8 wherein said pair of flanges/ribs includes a rib vertically disposed on said exterior shell of said vessel.

* * * * *